United States Patent
Lievois et al.

(10) Patent No.: US 8,274,041 B2
(45) Date of Patent: Sep. 25, 2012

(54) WATER DETECTION AND 3-PHASE FRACTION MEASUREMENT SYSTEMS

(75) Inventors: John Lievois, Houston, TX (US); Espen S. Johansen, Humble, TX (US); Babajide Adejuyigbe, Porter, TX (US)

(73) Assignee: Weatherford/Lamb, Inc., Houston, TX (US)

( * ) Notice: Subject to any disclaimer, the term of this patent is extended or adjusted under 35 U.S.C. 154(b) by 0 days.

(21) Appl. No.: 13/250,287

(22) Filed: Sep. 30, 2011

(65) Prior Publication Data

US 2012/0080587 A1    Apr. 5, 2012

Related U.S. Application Data

(63) Continuation of application No. 12/947,586, filed on Nov. 16, 2010, now Pat. No. 8,039,793, which is a continuation of application No. 11/625,427, filed on Jan. 22, 2007, now Pat. No. 7,834,312, which is a continuation-in-part of application No. 11/065,489, filed on Feb. 24, 2005, now Pat. No. 7,233,001.

(51) Int. Cl.
    *G01V 5/08*    (2006.01)
(52) U.S. Cl. .................................... 250/269.1
(58) Field of Classification Search ..... 250/269.1–269.8
    See application file for complete search history.

(56) References Cited

U.S. PATENT DOCUMENTS

| | | |
|---|---|---|
| 3,281,597 A | 10/1966 | Greenberg |
| 4,210,809 A | 7/1980 | Pelavin |
| 4,523,460 A | 6/1985 | Strickler et al. |
| 4,840,706 A | 6/1989 | Campbell |
| 5,166,747 A | 11/1992 | Schroeder et al. |
| 5,239,860 A | 8/1993 | Harris et al. |
| 5,266,800 A | 11/1993 | Mullins |
| 5,331,156 A | 7/1994 | Hines et al. |
| 5,729,013 A | 3/1998 | Bergren, III |
| 5,939,717 A | 8/1999 | Mullins |
| 6,076,049 A | 6/2000 | Lievois et al. |
| 6,265,713 B1 | 7/2001 | Berard et al. |
| 6,292,756 B1 | 9/2001 | Lievois et al. |
| 6,437,326 B1 | 8/2002 | Yamate et al. |

(Continued)

FOREIGN PATENT DOCUMENTS

EP    1325310    7/2003

(Continued)

OTHER PUBLICATIONS

Roy et al., "Infrared detection of chlorinated hydrocarbons in water at ppb level of concentrations," 2002, Water Research, vol. 36, pp. 1902-1908.*

(Continued)

*Primary Examiner* — Kiho Kim

(74) *Attorney, Agent, or Firm* — Patterson & Sheridan, L.L.P.

(57) ABSTRACT

Methods and apparatus enable monitoring a hydrocarbon well for water within a flow stream of the well. A water detector includes a light source for emitting into a flow stream infrared light that includes a water absorbent wavelength band. A detector detects attenuation of the water absorbent wavelength band upon the infrared radiation passing through at least a portion of the flow stream. The water detector outputs a presence of water and/or a phase fraction or quantification of water as determined based on the attenuation. Detecting attenuation of a substantially transmissive wavelength band with respect to water simultaneously with detection of the attenuation of the water absorbent wavelength band can enable correction for non-wavelength dependent attenuation.

19 Claims, 7 Drawing Sheets

U.S. PATENT DOCUMENTS

| | | |
|---|---|---|
| 7,067,459 B2 | 6/2006 | Pakulski et al. |
| 7,233,001 B2 | 6/2007 | Lievois et al. |
| 7,834,312 B2 | 11/2010 | Lievois et al. |
| 8,039,793 B2 | 10/2011 | Lievois et al. |
| 2002/0007952 A1 | 1/2002 | Vann |
| 2003/0056581 A1 | 3/2003 | Turner et al. |
| 2003/0106993 A1 | 6/2003 | Chen et al. |
| 2003/0155152 A1 | 8/2003 | Dybdahl |
| 2004/0056197 A1 | 3/2004 | Davidson et al. |
| 2004/0069942 A1 | 4/2004 | Fujisawa et al. |
| 2005/0094921 A1 | 5/2005 | DiFoggio et al. |
| 2006/0092423 A1 | 5/2006 | Servaites et al. |
| 2008/0135761 A1 | 6/2008 | Lievois et al. |

FOREIGN PATENT DOCUMENTS

| | | | |
|---|---|---|---|
| JP | 09318526 B2 | 12/1997 | |
| WO | 2004095010 A1 | 11/2004 | |
| WO | 2006129054 B1 | 7/2006 | |

OTHER PUBLICATIONS

Nagali et al., "Design of a Diode-Laser Sensor to Monitor Water Vapor in High-Pressure Combustion Gases," Dec. 1997, Applied Optics, vol. 35, No. 36, pp. 9518-9527.

PCT International Search Report from International Application No. PCT/US2008/051628 dated Jun. 2, 2008.

British Examination Report dated May 16, 2008.

British Examination Report dated Jan. 7, 2009.

GB Preliminary Examination and Search Report for Application No. 0603842.6 dated Jun. 30, 2006.

* cited by examiner

US 8,274,041 B2

WATER DETECTION AND 3-PHASE FRACTION MEASUREMENT SYSTEMS

CROSS-REFERENCE TO RELATED APPLICATIONS

This application is a continuation of co-pending U.S. patent application Ser. No. 12/947,586, filed Nov. 16, 2010, which is a continuation of U.S. patent application Ser. No. 11/625,427, filed Jan. 22, 2007, now U.S. Pat. No. 7,834,312, issued Nov. 16, 2010, which is a continuation-in-part of U.S. patent application Ser. No. 11/065,489, filed Feb. 24, 2005, now U.S. Pat. No. 7,233,001, issued Jun. 19, 2007, which are all herein incorporated by reference.

BACKGROUND OF THE INVENTION

1. Field of the Invention

Embodiments of the invention generally relate to flow analysis.

2. Description of the Related Art

Oil and/or gas operators periodically measure water/oil/gas phase fractions of an overall production flow stream in order to aid in improving well production, allocating royalties, properly inhibiting corrosion based on the amount of water and generally determining the well's performance. Various approaches for analyzing the phase fraction of such flow streams exist and include full or partial phase separation and sensors based on capacitive, density and microwave measurements. However, known measurement techniques suffer from their own unique drawbacks and/or limitations.

Wells often produce water along with hydrocarbons during normal production from a hydrocarbon reservoir within the earth. The water resident in the reservoir frequently accompanies the oil and/or gas as it flows up to surface production equipment. Onset of water in gas wells and wet gas wells introduces the prospect of ice-like hydrate formation, which can plug lines and create unsafe flowing conditions. Water in the production flow at low temperatures such as less than 15° C. as occurs in seawater applications may cause formation of the hydrates depending on volume and pressure of the flow. Furthermore, gas wells that are often high rate produce large pressure drops across chokes and flow area changes. At these locations, Joule Thompson cooling can reduce temperatures significantly which may result in severe hydrate problems in a matter of hours or even minutes if water is present. Serious problems result once the hydrates form and block or limit flow. Continuous measurement of phase fraction rather than, for example, monthly testing can improve operations such as hydrate prevention as well as reservoir management and allocations.

Some approaches utilize chemical injection to inhibit gas hydrate formation in case of any potential water breakthrough that may not be detected. However, cleaning and treatment procedures required at surface to remove the hydrate inhibitor along with high costs of the inhibitor itself contribute to production expenses. Therefore, injection of methanol as an exemplary hydrate inhibitor unnecessarily increases costs when preformed even if water is not present or when done at levels beyond that required based on the water that is present.

Therefore, there exists a need for an improved water detector and overall phase fraction measurement to enable, for example, flow assurance, improved reservoir management, and improved allocation from a producing well. There exists a further need for an improved infrared optical detector, such as a water detector that provides the flow assurance or other flow related information with improved sensitivity and accuracy.

SUMMARY OF THE INVENTION

Methods and apparatus generally relate to monitoring a hydrocarbon well for water within a flow stream of the well. A water detector includes a light source for emitting into a flow stream infrared light that includes a water absorbent wavelength band. A detector measures the transmitted light of the water absorbent wavelength band passing through at least a portion of the flow stream. The water detector outputs a presence of water and/or a phase fraction or quantification of water as determined based on the attenuation. Measuring attenuation of a substantially transmissive wavelength band with respect to water simultaneously with measurement of the attenuation of the water absorbent wavelength band can enable correction for non-wavelength dependent attenuation. Some embodiments may include a hydrocarbon absorbent wavelength band and/or, in some instances, a second water absorbent peak that can differentiate water from alcohols.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

FIG. 3A is an end view of a connector taken across line 3A-3A in FIG. 3.

DETAILED DESCRIPTION

Embodiments of the invention generally relate to water detectors that utilize infrared optical analysis techniques. While the water detector is illustrated herein as part of a test system that is also capable of detecting phase fractions from a flow stream being produced from a well, use of the water detector includes various other applications and can provide moisture detection without requiring water quantification or such further phase fraction detection. For example, other industries such as pharmaceutical, food, refinery, chemical, paper, pulp, petroleum, gas, mining, minerals and other fluid processing plants often utilize flow assurance systems in order to detect whether or not water is present at all.

Figure 1:
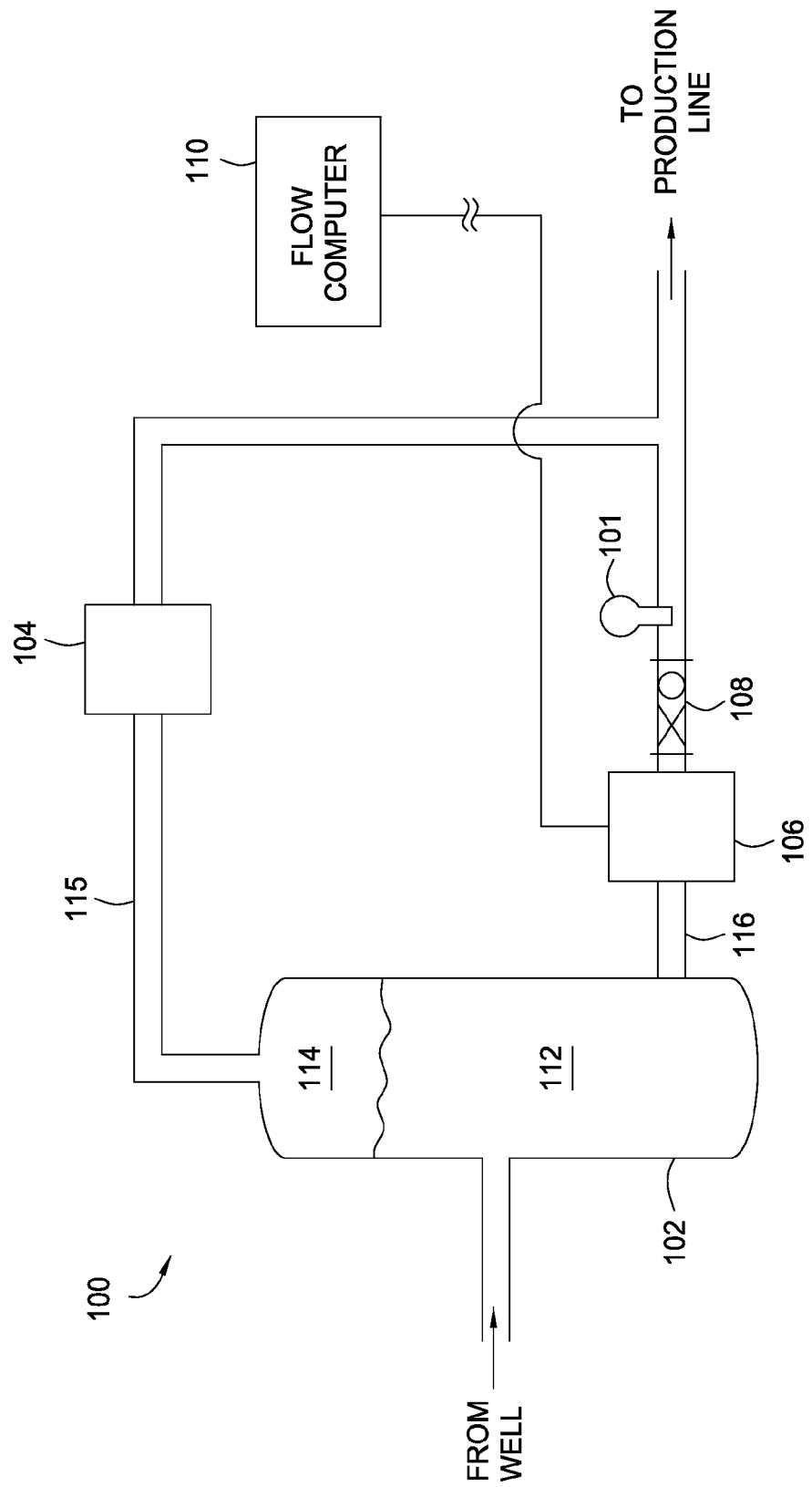
FIG. 1 is a schematic diagram of a well testing system that includes an infrared phase fraction meter in accordance with embodiments of the invention.

FIG. 1 shows a well testing system 100 including an infrared phase fraction meter 101 in accordance with embodiments of the invention. U.S. Pat. Nos. 6,076,049 and 6,292,756, which are herein incorporated in their entirety, further describe examples of infrared water fraction systems such as the testing system 100. The well testing system 100 takes a production flow directly from a well or from a common gathering station (not shown) that provides a manifold to direct one well at a time to the testing system 100 while production from a plurality of other wells is directed to a production line by bypassing the testing system 100. The testing system 100 includes a separator 102, a gas flow meter 104, a liquid flow meter 106, an optional mixer 108, the infrared phase fraction meter 101 and a flow computer 110. For some embodiments and applications, the separator 102 and the gas flow meter 104 may not be required as will be apparent from the following discussion. The separator 102 divides the production flow into a liquid portion 112 that includes water content and oil content of the production flow and a gas portion 114 that includes gas content of the production flow.

The gas flow meter 104 measures flow through a gas stream 115. On the other hand, a flow stream 116 passes from the liquid portion 112 of the separator 102 to the liquid flow meter 106 and the infrared phase fraction meter 101. The flow stream 116 often includes some gases even after being separated and may even be a fluid stream that has not been separated. The liquid flow meter 106 detects an overall flow rate of the flow stream 116 without differentiating phases making up the flow stream 116. Accordingly, determining a flow rate of individual phases requires determining what percent of the flow stream 116 that each phase makes up. In one embodiment, the infrared phase fraction meter 101 detects a water cut of the flow stream 116. Thus, the phase fraction meter 101 along with the liquid flow meter 106 enables calculation of the flow rate of water and oil phases.

In general, the mixer 108 includes any structure or device capable of making the flow stream 116 more homogenous prior to being sampled by the infrared phase fraction meter 101. For example, a set of axially spaced veins or blades disposed within a flow path of the flow stream 116 forms a static mixer for use as the mixer 108. The phase fraction meter 101 may not require incorporation of the mixer 108 within the flow stream 116 as would be the case when the flow stream 116 is sufficiently mixed.

Figure 2:
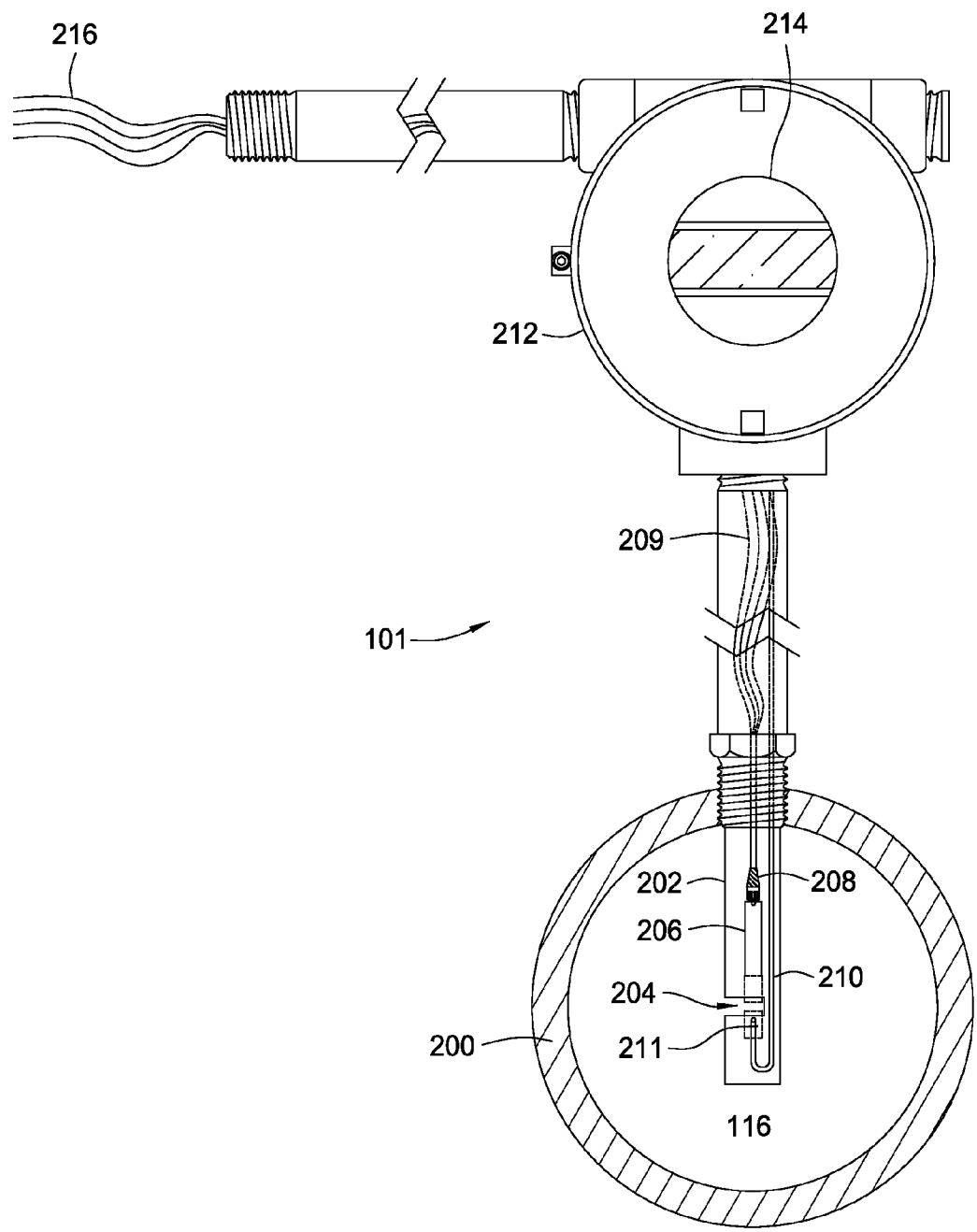
FIG. 2 is a partial section view of an infrared phase fraction meter having a probe end inserted into a pipe.

FIG. 2 illustrates the phase fraction meter 101 disposed on a pipe 200 that carries the flow stream 116 therein. A probe end 202 of the meter 101 inserts into the pipe 200 such that a sampling region 204 is preferably located in a central section of the pipe 200. A body portion 212 of the meter 101 couples to the probe end 202 and houses electronics (not shown) and an optional local display 214 outside of the pipe 200. The meter 101 further includes a broad band infrared source 211 coupled to a power supply line 210 and located on an opposite side of the sampling region 204 from a collimator 206 that is coupled to the body portion 212 by optical outputs 209 connected thereto by a common connector 208 such as a Sub-Miniature Version A (SMA) connector. For some embodiments, the source 211 includes a tungsten halogen lamp capable of emitting light in a range of wavelengths that includes particular wavelengths selected for interrogation as discussed in detail below. Input and output wiring connections 216 lead from the body portion 212 of the meter 101 for providing power to the meter 101 and communication with the flow computer 110 (shown in FIG. 1) and optionally the liquid flow meter 106 (shown in FIG. 1). When the phase fraction meter 101 is connected to the flow meter 106, the phase fraction meter 101 may capture flow data from the flow meter 106 as a 4-20 milliamp or frequency based signal that can be processed and made accessible to the flow computer 110, for example, via the wiring connections 216 using an industry standard protocol, such as Modbus.

Figure 3:
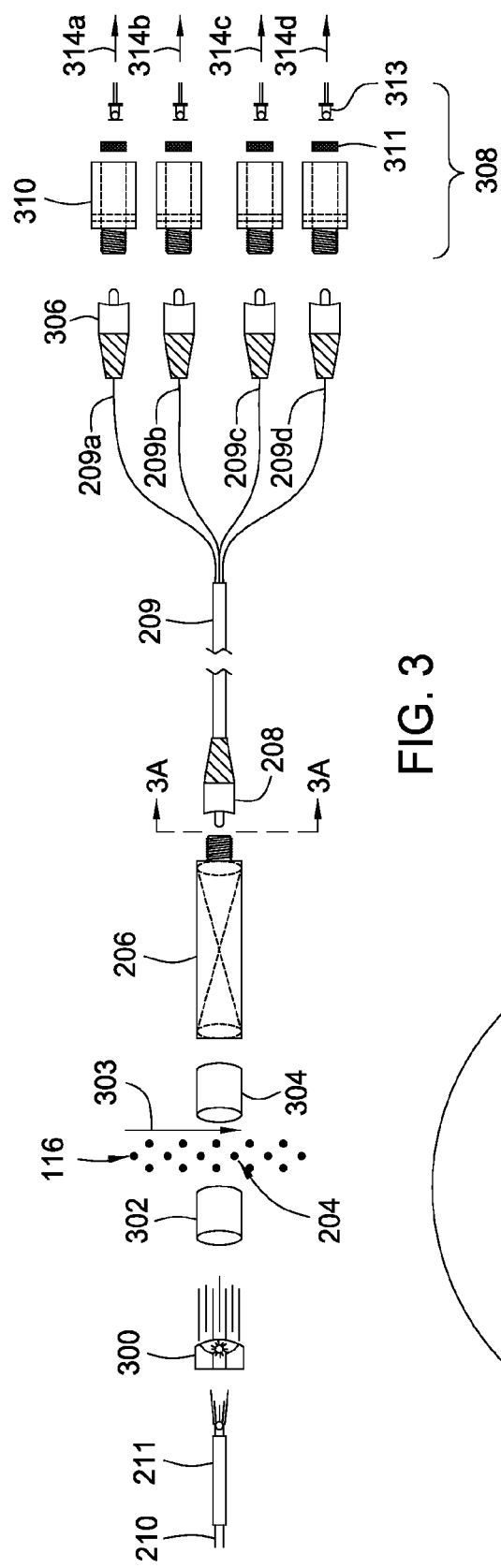
FIG. 3 is an exploded view of internal components of the infrared phase fraction meter illustrated in FIG. 2.

FIG. 3 illustrates internal components of the infrared phase fraction meter 101 in an exploded view. These components include the source 211, a parabolic reflector 300 for directing light from the source 211, first and second sapphire plugs 302, 304, the collimator 206 and the optical outputs 209 that couple the collimator 206 to infrared filters 308. An area between the sapphire plugs 302, 304 defines the sampling region 204 where fluid of the flow stream 116 flows across as indicated by arrow 303.

In operation, light from the source 211 passes through the first sapphire plug 302 and through the fluid of the flow stream 116 where the light is attenuated prior to passing through the second sapphire plug 304. Unique absorption characteristics of the various constituents of the flow stream 116 cause at least some of the attenuation. The collimator 206 adjacent the second sapphire plug 304 focuses and concentrates the attenuated light into optical outputs 209 via the common connector 208. The optical outputs 209 typically include a multitude of optical fibers that are divided into groups 209a-d. Utilizing one type of standard connector, eighty-four fibers pack within the common connector 208 such that each of the four groups 209a-d comprise a total of twenty one fibers. However, the exact number of fibers and/or groups formed varies for other embodiments.

As illustrated in FIG. 3A by end view 207, the fibers within each of the groups 209a-d may be arranged to avoid sampling at discrete zones which may be affected by inconsistency of the source 211 and/or isolated variations within the flow stream 116. Specifically, each individual fiber receives light transmitted across a discrete light path through the fluid that is different from a light path of adjacent fibers. The end view 207 schematically illustrates fiber ends A, B, C, D corresponding to groups 209a, 209b, 209c, 209d, respectively, and arranged such that each quadrant of the end view 207 includes fibers from all groups 209a-d. For example, one fiber of the group 209a receives light passing through a path on the left side of the sampling region 204 while another fiber of the group 209a receives light passing through a path on the right side of the sampling region 204 such that the combined light from both fibers is detected. Accordingly, this arrangement may reduce errors caused by making a measurement at only one discrete location by effectively averaging the light received from all fibers within the group 209a.

Each of the four groups 209a-d connects to a respective housing 310 of one of the infrared filters 308 via a connector 306 such as an SMA connector. Each of the infrared filters 308 includes the housing 310, a narrow band pass filter 311 and a photo diode 313. The photo diode 313 produces an electrical signal proportional to the light received from a respective one of the groups 209a-d of the optical outputs 209 after passing through a respective one of the filters 311. Preferably, a logamp circuit (not shown) measures the electrical signals to give up to five decades of range. Each of the filters 311 filters all but a desired narrow band of infrared radiation. Since each of the filters 311 discriminate for a selected wavelength band that is unique to that filter, each of the groups 209a-d represent a different channel that provides a total attenuation signal 314 indicative of the total attenuation of the light at the wavelengths of that particular filter. Thus, the signals 314a-d from the four channels represent transmitted radiation at multiple different desired wavelength bands.

If only one wavelength is interrogated without comparison to other wavelengths, absorption based attenuation associated with that one wavelength cannot be readily distinguished from other non-absorption based attenuation that can introduce errors in an absorption measurement. However, using multiple simultaneous wavelength measurements provided by the signals 314a-d from the different channels enables non-wavelength dependent attenuation, such as attenuation caused by common forms of scattering, to be subtracted out of the measurements. An appropriate algorithm removes these non-absorption background influences based on the fact that the non-wavelength dependent attenuation provides the same contribution at each wavelength and thence at each channel regardless of wavelength dependent absorption. Thus, comparing the signals 314a-d from each channel at their unique wavelengths enables correction for non-wavelength dependent attenuation.

Additionally, selection of the filters 311 determines the respective wavelength for each of the multiple simultaneous wavelength measurements associated with the signals 314a-d from the different channels. Accordingly, the different channels enable monitoring of wavelengths at absorbent peaks of the constituents of the flow stream 116, such as water absorbent peaks in addition to oil absorbent peaks, based on the wavelengths filtered. To generally improve resolution, a minute change in the property being measured ideally creates a relatively large signal. Since the relationship between concentration and absorption is exponential rather than linear, large signal changes occur in response to small concentration changes of a substance when there is a low cut or fraction of the substance being measured based on attenuation of the signal from the channel(s) monitoring the wavelengths associated with an absorbent peak of that substance. In contrast, small signal changes occur in response to concentration changes of the substance when there is a high cut of the substance being measured by the same channel(s).

Accordingly, the different channels provide sensitivity for the meter across a full range of cuts of the substance within the flow, such as from 0.0% to 100% phase fraction of the substance. For example, channel(s) with wavelengths at water absorbent peaks provide increased sensitivity for low water fractions while channel(s) with wavelengths at oil absorbent peaks provide increased sensitivity for high water fractions. Thus, the channel(s) with the highest sensitivity can be selected for providing phase fraction results or averaged with the other channels prior to providing the results in order to contribute to the sensitivity of the meter.

Another benefit of the multiple simultaneous wavelength measurements provided by the signals 314a-d from the different channels includes the ability to accurately calibrate the meter 101 with a small amount of pure fluid. Thus, calibration of the meter 101 does not require a reference cut. Selection of wavelengths as disclosed herein for the channels reduces sensitivity to different types of oil in order to further simplify calibration. For example, oils which are light in color or even clear have an optimal absorption peak around a wavelength of 1,750 nanometers, but black oils have stronger absorption around a wavelength of 1,000 nanometers. If two of the four channels include filters at these wavelengths, then the algorithm can determine the optimal choice at the calibration stage rather than requiring a hardware change for different oil types.

Figure 4:
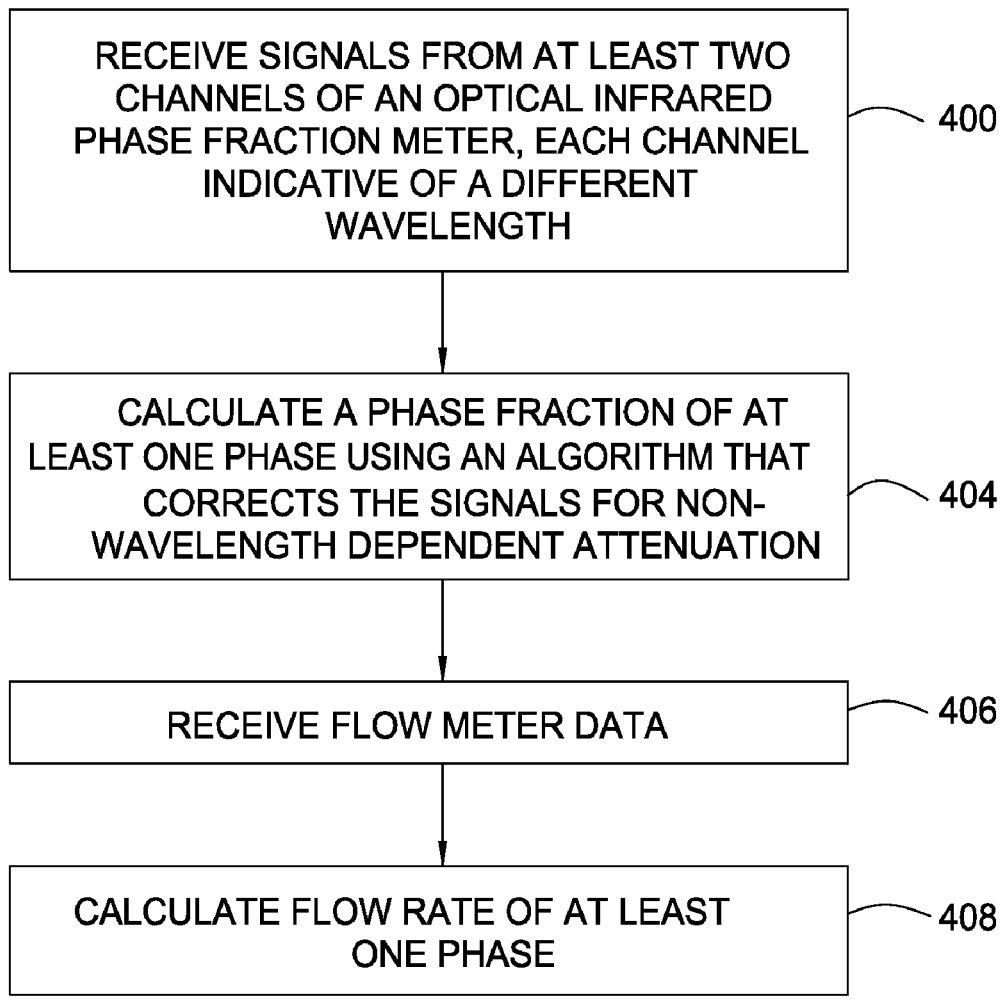
FIG. 4 is a flow chart of a flow processing technique performed by the phase fraction meter and a flow computer of FIG. 1.

FIG. 4 shows a flow chart of a flow processing technique performed by the phase fraction meter 101 and/or the flow computer 110 (shown in FIG. 1) after emitting infrared radiation into the flow stream 116. The processing begins at a step 400 where electronics receive signals 314a-b from at least two channels of the phase fraction meter 101. In a step 404, an algorithm calculates a phase fraction of at least one phase due in part on absorption readings for "pure" substances made in a calibration step (not shown). The algorithm corrects the signals for non-wavelength dependent attenuation based on these influences effecting signals from each channel indiscriminately such that the non-wavelength dependent attenuation drops out in the solution of simultaneous equations. For example, a water cut of the flow stream 116 can be calculated by averaging or otherwise combining results from non-homogeneous linear equations calculated for each channel, wherein the equations include detector photocurrent values corrected for non-wavelength dependent attenuation, an absorption constant, and hardware constants. The following equation defines an exemplary equation that may be used for calculating the water cut ($C_w$) as measured by a single channel:

$$I_i = \beta(I_{oi})e^{-(a_{Oi}x_O + a_{Wi}x_W)} \quad (1)$$

$$x_O + x_W = 1 \quad (2)$$

where $I_i$ represents transmitted light at frequency band i, $\beta$ represents a frequency independent attenuation coefficient, $I_{Oi}$ represents incident light at frequency band i, $\alpha_{Oi}$ represents the absorption coefficient of the oil at frequency band i, $\alpha_{Wi}$ represents the absorption coefficient of the water at frequency band i, $x_O$ represents the fraction of the path length occupied by oil, and $x_W$ represents the fraction of the path length occupied by water. $x_W$ is equivalently the water cut "$C_W$" of the mixture. Equations 1 and 2 contain three unknowns, $x_O$, $x_W$, and $\beta$. A minimum of two frequencies are therefore required to solve for $C_W$:

$$C_W = x_W = \frac{\ln\left[\frac{I_2}{I_1}\right] - (a_{O1} - a_{O2})}{(a_{W1} - a_{W2}) - (a_{O1} - a_{O2})} \quad (3)$$

After receiving data from the flow meter 106 as indicated in a step 406, the flow computer calculates a flow rate of the at least one phase in a step 408.

Figure 5:
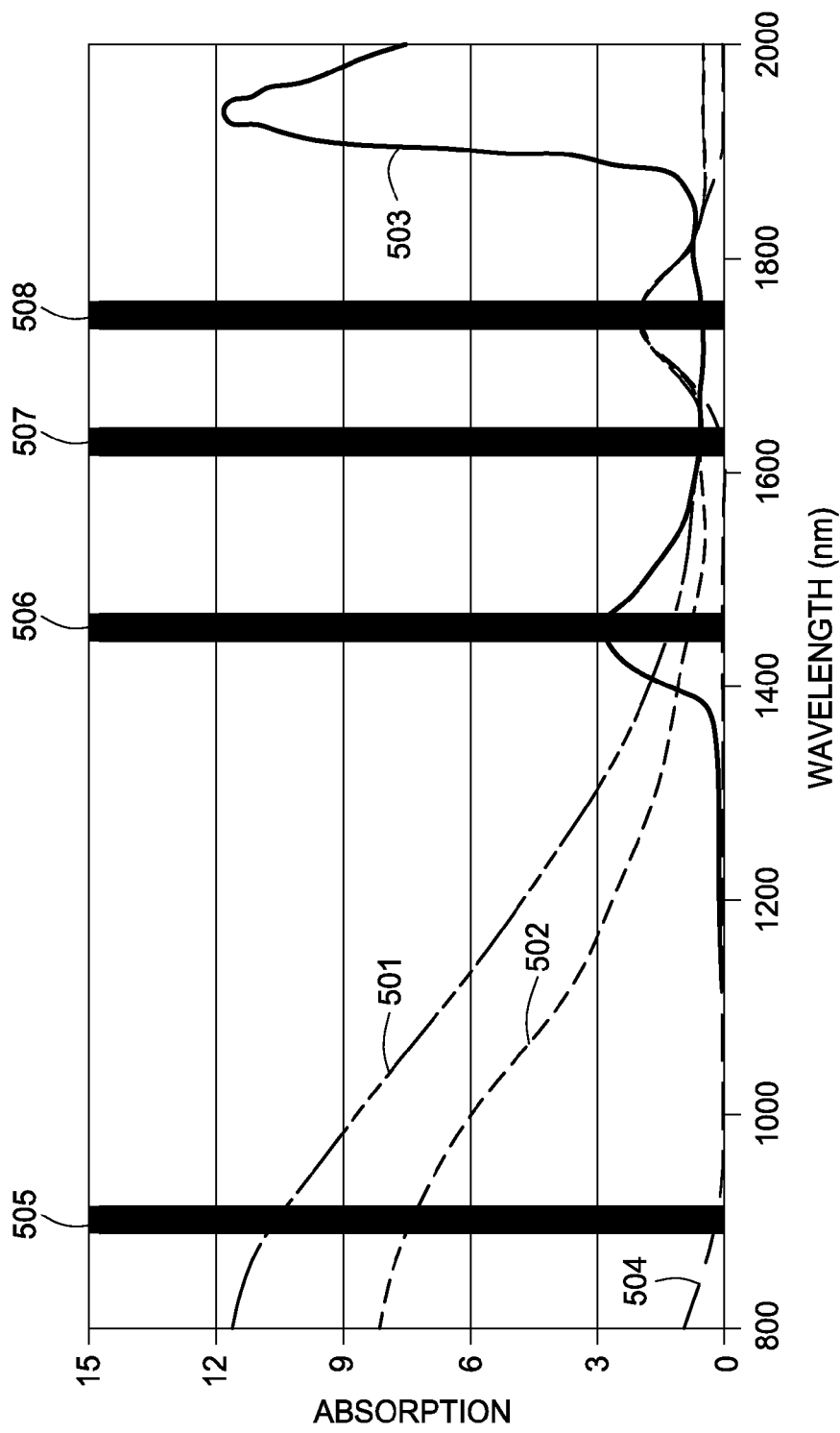
FIG. 5 is a graph illustrating absorption of two types of oil, water and condensate for an infrared region and wavelengths thereof selected for interrogation via channels of an infrared phase fraction meter.

FIG. 5 illustrates a graph of absorption verses wavelength for two types of oil indicated by curves 501, 502, water represented by curve 503 and condensate denoted by curve 504 for an infrared region. Gas provides relatively zero absorption at typical test line pressures and has accordingly been omitted from the graph. The graph shows four preferred wavelength bands 505-508 for filtering by the filters 311 in order to provide the four channels of the phase fraction meter 101. Other wavelength bands may be selected without departing from the scope of the invention. The phase fraction meter 101 essentially ignores salinity changes since typical salinity levels have negligible effect on water absorption over the spectral region of interest. Additionally, lack of significant absorption by gas makes the meter 101 substantially insensitive to free gas in the fluid stream 116.

In general, a first wavelength band 505 includes wavelengths within a range of approximately 900 nanometers (nm) to 1200 nm, for example about 950 nm, where there is an oil absorbent peak. A second wavelength band 506 includes wavelengths centered around 1450 nm where there is a water absorbent peak. A trough around 1650 nm provides another interrogation region where a third wavelength band 507 generally is centered. A fourth wavelength band 508 generally includes a peak centered about 1730 nm that is fundamentally associated with carbon-hydrogen bonds of the oil 501, 502 and the condensate 504. The substantial similarities and/or differences in the absorption of the different phases at each of the bands 505-508 further enables their differentiation from one another with the phase fraction meter 101.

For some embodiments, the flow meter 106 may only provide a mass flow rate instead of a volumetric flow rate. In these embodiments, the phase fraction meter 101 measures the phase fraction as discussed above. The phase fractions of the oil and water are then multiplied by their respective known densities and summed to provide the density of the combined fluid since the gas density is minimal. The mass flow rate is then divided by this calculated density of the combined fluid to provide an accurate volumetric flow rate.

Exemplary Flow Reqimes/Applications

Different flow models or regimes may be useful for flow processing depending upon the particular application. For example, in an application, where gas and water travel at different velocities or where the oil travels in slugs through the pipe, a flow model can take these flow conditions into account. Furthermore, the following sections describe various additional methodologies for making measurements of different flow regimes using the meter shown herein. Selecting the appropriate algorithm for given conditions can improve accuracy of the measurements.

Water cut measurements (i.e., water cut only (water/total liquid ratio) with no measure of the gas phase volume) may be made throughout a wide range of free gas phase content in the stream. Three exemplary flow regimes may be defined as i) dispersed gas bubble in liquid; ii) gas-liquid slugs; and iii) dispersed liquid in gas. The first two flow regimes cover flows where about 0-95% gas volume fraction (GVF) exists while the last regime includes about 95-99.99% GVF.

Full Range Water Cut (0-100%) with Three Phase Streams (Oil, Water, Gas) where Gas can Represent about 0-95% Gas Volume Fraction (GVF).

Absorbance measurements performed using the meter correspond to a function which may be defined as:

$$A_i = a_{oi}x_o + a_{wi}x_w + S \qquad (4)$$

where:
 $A_i$=total absorbance at wavelength i and includes chemical (absorption) and physical (scattering) effects;
 $a_{oi}$=absorption coefficient for oil at wavelength i;
 $a_{wi}$=absorption coefficient for water at wavelength i;
 $x_o$=pathlength of oil;
 $x_w$=pathlength of water; and
 S=scatter contribution to overall absorbance (wavelength independent).

Instead of utilizing a fixed path length (e.g., Equation 2) in determining water cut, making three separate absorbance measurements for three different wavelengths enables solving for three unknowns ($x_o$, $x_w$, and S) in Equation 4. This allows for the potential of increased effective pathlength due to scattering. This approach works for flow regimes without gas or with the dispersed gas bubbles in liquid (flow regime i) to enable calculation of the water cut based on the pathlength of water $x_w$ relative to the total pathlength $X_w + X_o$.

For the gas-liquid slugs (flow regime ii), the meter suspends analysis when recognized, due to the absorbance measurements, that the sensor gap is filled with a gas continuous mix (e.g. all gas or dispersed liquid in gas). The meter bases the water cut determination on measurements taken at intervals when the gap is filled with a liquid continuous mix (e.g., all liquid or dispersed gas bubble in liquid). Therefore, applying Equation 4 as described above during these selected intervals associated with liquid slugs passing across the meter enables an improved calculation for the water cut, which is independent of the quantity of gas and hence the suspended intervals.

Full Range Water Cut (0-100%) with Three Phase Streams (Oil, Water, Gas) where Gas can Represent about 95-99.99% GVF and Three Phase Fraction Measurement for Full Range Water Cut (0-100%) and 95-99.99% GVF.

With respect to the dispersed liquid in gas (flow regime iii), a flow with about 95-99.99% GVF defines a flow stream that is gas continuous and is in the "wet gas" region. If three wavelengths are selected where gas has no absorption, then Equation 4 above can be used to solve for water cut. If a wavelength is used where gas has some absorption (i.e. high pressure methane at 1730 nm), then the function representing the absorbance measured may be modified to:

$$A_i = a_{oi}x_o + a_{wi}x_w + a_{gi}x_g + S \qquad (5)$$

where:
 $a_{gi}$=gas absorption coefficient at wavelength i; and
 $x_g$=pathlength of gas.

Solving for the water cut using Equation 5 requires making absorbance measurements at four wavelengths due to the pathlength of gas $x_g$ representing an additional unknown. Further, the solution of Equation 5 also yields phase fraction for oil, water and gas individually.

Three Phase Fraction Measurement for Full Range Water Cut (0-100%) and 0-95% GVF.

A further extension of the application of Equation 4 above enables determination of three phase fraction measurements of a flow stream. Solution of Equation 4 provides water content and oil content but not the gas content. For the dispersed gas bubble in liquid (flow regime i), the gas content can be estimated as:

$$x_g = 1 - x_o - x_w \qquad (6)$$

where the path lengths have been normalized. With respect to the gas-liquid slugs (flow regime ii), the amount of time the sensor gap is gas continuous relative to total time indicates the gas content. In other words, measuring gas slugs based on the percentage of time analysis is suspended enables calculation of the gas content for flow conditions with the gas-liquid slugs (flow regime ii).

Three Phase Fraction-Four Component Measurement for Full Range Water Cut (0-100%) and 95-99.99% GVF.

As described heretofore, embodiments of the invention enable three phase fraction measurements (oil, water, gas) when the flow stream is gas continuous with dispersed liquid (flow regime iii). Furthermore, the flow stream can contain an injected chemical such as methanol to act as a hydrate inhibitor. The chemical may be miscible in both the hydrocarbon and aqueous phases.

Using n+1 wavelengths or more enables calculating the concentrations of n components even if one or more of the components are not in separate phases, such as the methanol. Based on the teachings herein, the absorption coefficients must not be identical for any two components over the n+1 wavelengths. For water and methanol (or other alcohols), selection of 1450 nm and 1950 nm for analysis insures different absorption coefficient sets.

For some embodiments, concentration measurements in any GVF may be made for various hydrocarbon components to determine calorimetric measurements of fluid flow. For example, gas composition analysis may involve selecting wavelengths to be analyzed for differentiating methane from heavier hydrocarbons such ethane or propane. Further, oil composition analysis may similarly rely on wavelength selection to facilitate calorimetric measurement thereof.

Detecting Water Presence

Figure 6:
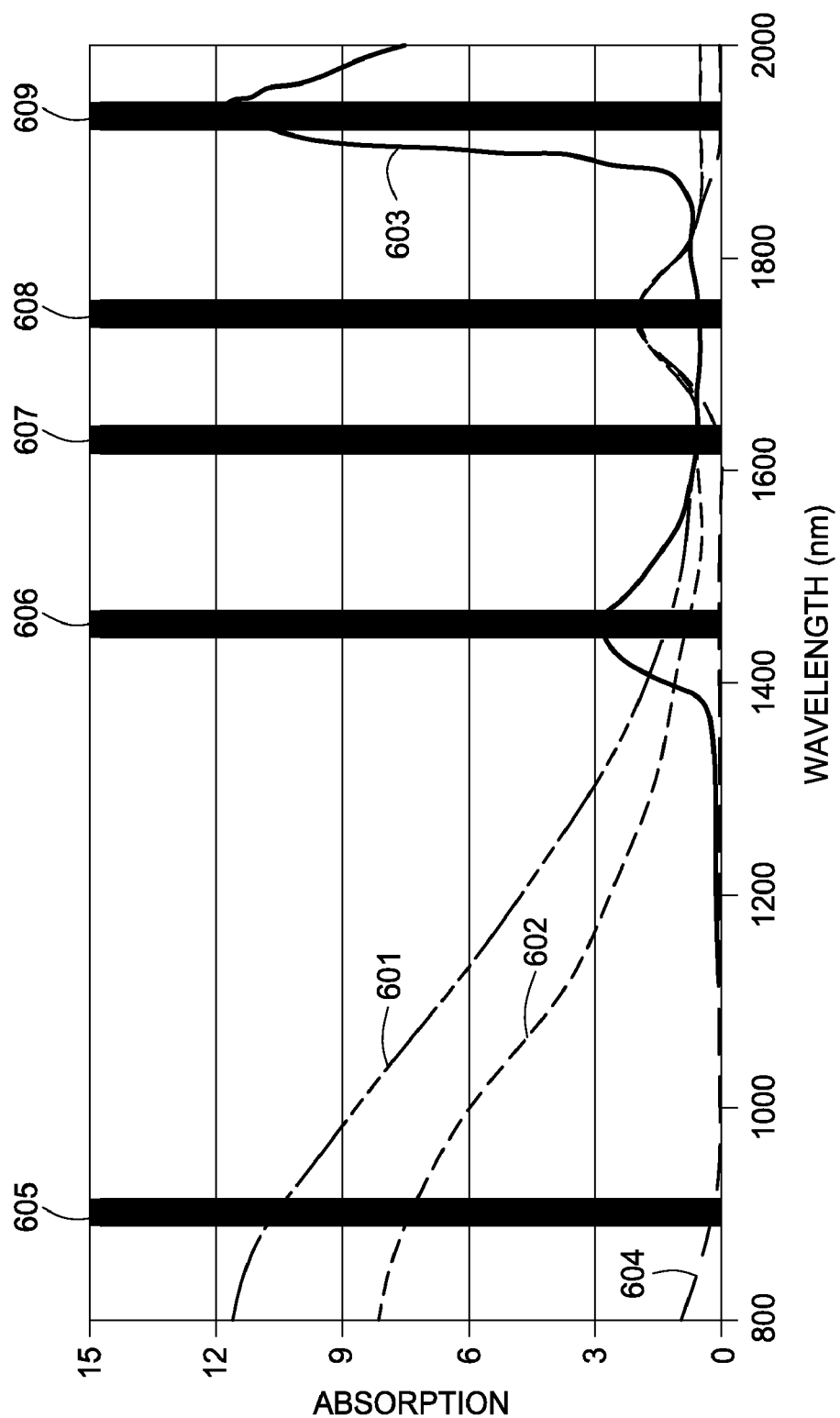
FIG. 6 is a graph illustrating absorption of two types of oil, water and condensate for an infrared region and wavelengths of the infrared region selected for interrogation via channels of an infrared water detector.

Like FIG. 5, FIG. 6 shows a graph of absorption verses wavelength for oil curves 601, 602, water curve 603 and condensate curve 604 for an infrared region. A water detector enables performing spectral analysis of sensitive water wavelength peaks along the water curve 603 in order to provide flow assurance or moisture detection. For some embodiments, the water detector includes identical components as the infrared phase fraction meter 101 (shown in FIGS. 2-3A), which can thereby be operated as the water detector and/or the phase fraction meter. In other words, the term "water detector" as used herein can but does not necessarily enable measurement of phase fractions including quantifications regarding water fractions.

Components of the water detector can be adapted for use in the wellbore or subsea for some embodiments such as applications where immediate water breakthrough information is required. Further, distance across a sampling region of the water detector can be variable, can extend across an entire cross-section of a conduit, or can define two or more different path lengths across the sampling region. Selecting the appropriate path length for a particular fluid flow can thereby improve sensitivity of the water detector. For example, selecting a maximum path length due to the distance across the sampling region extending across the entire cross-section of the conduit can improve sensitivity where the mixture is predominantly gas and hence substantially transmissive.

As shown in FIG. 6, the graph shows examples of first, second, third, fourth and fifth wavelength bands 605-609 for optional filtering by filters of the water detector in order to provide channels of the water detector. Since channels with wavelengths at water absorbent peaks provide increased sensitivity for low water fractions, the second wavelength band 606 selected around 1450 nm and/or the fifth wavelength band 609 selected around 1950 nm enable sensitive presence detection and/or quantified measurement of water. Absorption characteristics associated with H—O—H molecular bending occur at around 1950 nm such that water absorbs light in the fifth wavelength band 609. In addition, absorption characteristics due to O-H stretching occur at around 1450 nm such that both water and methanol absorb light in the second wavelength band 605.

For some embodiments, the water detector utilizes only one of the second and fifth wavelength bands 606, 609 or other wavelength bands also associated with absorption by water, in particular, bands that have absorption characteristics in water equivalent to or greater than the fifth wavelength band 609. Any absorption detected at the second or fifth wavelength band 606, 609 can thereby indicate a presence of water. The amount of absorption can correlate (e.g., Beer's Law) to the quantity of water present.

Concurrent measurements at wavelengths off water absorbent peaks such as one or more of the first, third and fourth wavelength bands 605, 607, 608 enables correcting signals indicative of absorbance measured at one or both of the second and fifth wavelength bands 606, 609 for non-wavelength dependent attenuation such as previously described herein. Signal attenuation results from water absorption, oil absorption or scattering since the gas phase is relatively non-absorbent. Accordingly, ratiometric based measurements utilizing the concurrent measurements enables quantifying and correcting for this scattering portion so the presence of water can be accurately detected and/or a water to oil ratio can be determined.

Monitoring of the fifth wavelength band 609 at around 1950 nm enables differentiation of water from any injected methanol used to inhibit hydrate formation since the methanol only has a carbon to hydroxyl bond that does not provide the same water molecule deformation that causes absorption at around 1950 nm. This ability to differentiate the methanol from water permits detection of the water even during hydrate inhibitor injection. Additionally, detection of the amount of water being produced enables determination of whether the hydrate inhibitor is sufficient given the quantity of the inhibitor selected to be injected.

In addition, monitoring the fifth wavelength band 609 or an equivalent band with respect to water absorption characteristics causes sufficient attenuation at concentrations of water even below 0.1% to enable use of the water detector for flow assurance in critical well applications where hydrate formation possibilities exist. Therefore, spectral analysis of the fifth wavelength band 609, for example, enables this low level moisture detection. However, other wavelength bands less absorbed by water than the fifth wavelength band 609 may be suitable for higher water concentrations once presence of water is known or determined such as by measurement of any attenuation at the fifth wavelength band 609, which attenuation may tend to absorb all input light at the fifth wavelength band 609 causing saturation that inhibits any further determinations based off readings associated with the fifth wavelength band 609.

Figure 7:
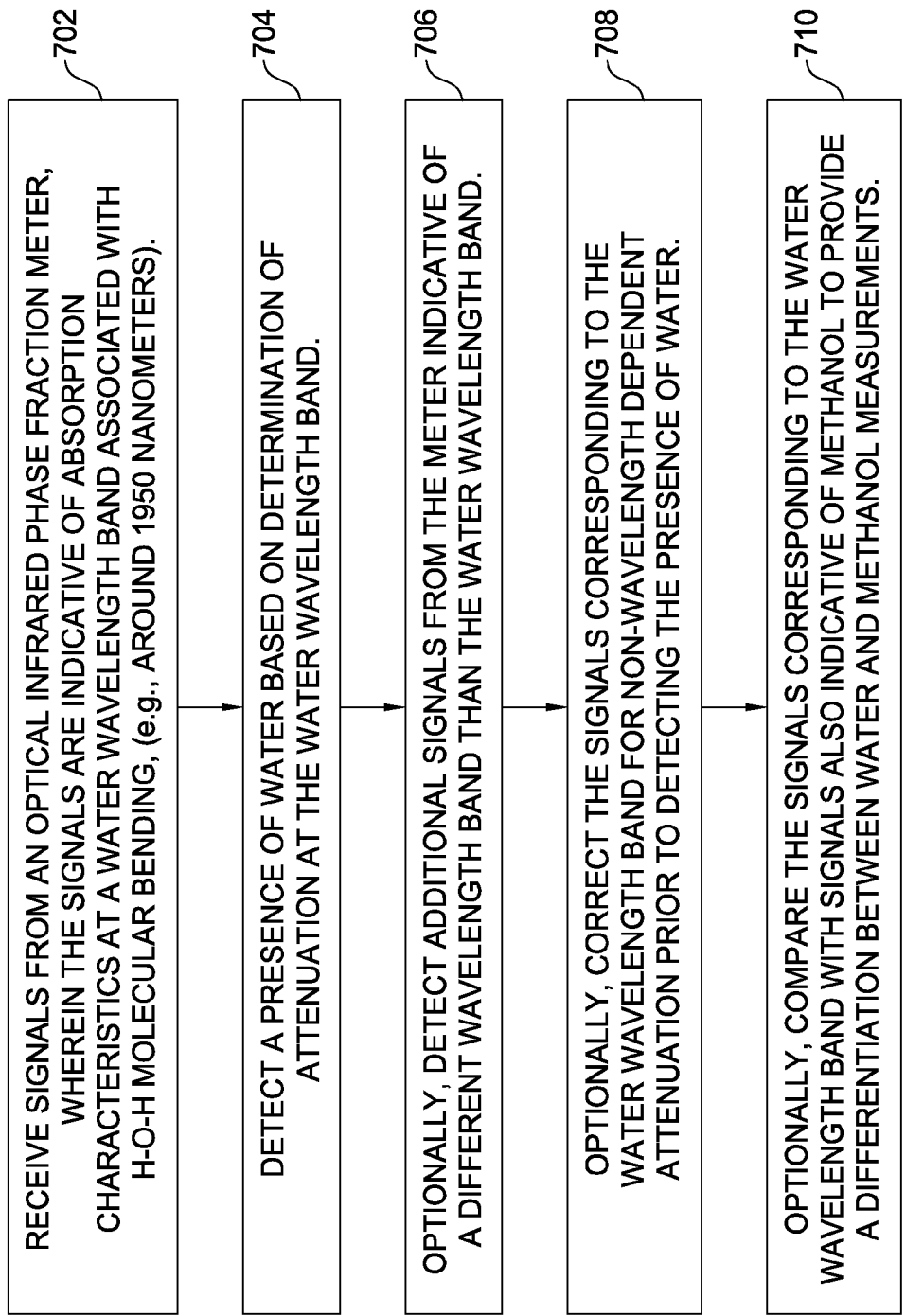
FIG. 7 is a flow chart of a flow processing technique to detect a presence of water utilizing the water detector.

FIG. 7 illustrates a flow chart of a flow processing technique to detect a presence of water utilizing the water detector. At signal receipt step 702, electronics receive signals from at least one channel of the water detector. The at least one channel corresponds to a water absorbent wavelength band such as the fifth wavelength band 609. An algorithm at detection step 704 identifies a presence of water and/or determines a quantification or phase fraction of the water based on absorbance readings from the signals. An alarm, visual output or automated corrective action can initiate upon detecting the water so that, for example, appropriate reductions in producing rate or methanol injections can be made.

Detection of signals corresponding to concurrent measurements at wavelengths off water absorbent wavelength peak(s) can occur at additional channel step 706. At correction step 708, an algorithm can correct the signals for non-wavelength dependent attenuation based on influences effecting signals from each channel indiscriminately such that the non-wavelength dependent attenuation drops out in the detection step 704. A methanol indicating step 710 can compare signals corresponding to the water absorbent wavelength band(s) with a signal that also corresponds to a methanol absorption band such as the second wavelength band 606. The comparison from the methanol indicating step 710 can enable differentiation between water and methanol measurements.

The preferred embodiments use the broad band source and the filters to isolate wavelengths associated with the channels. However, other embodiments of the phase fraction meter include separate narrow band sources, tunable filters, and/or a single source that is swept for the desired wavelengths of the channels.

While the foregoing is directed to embodiments of the present invention, other and further embodiments of the invention may be devised without departing from the basic scope thereof, and the scope thereof is determined by the claims that follow.

What is claimed is:

1. An optical water detector for monitoring a hydrocarbon well, comprising:
a source for emitting into a flow stream light that includes first and second wavelength bands associated with absorption by water, wherein the second wavelength band is less absorbed by water than the first wavelength band;
a detector configured to detect attenuation of the first wavelength band upon the light passing through at least a portion of the flow stream; and
an output indicative of a concentration of water as determined based on the attenuation of the first wavelength band, wherein the detector is configured to detect attenuation of the second wavelength band instead of or in addition to the first wavelength band when the concentration of water is higher than a certain level.

2. The water detector of claim 1, wherein the output is further indicative of a concentration of water as determined based on the attenuation of the first wavelength band.

3. The water detector of claim 2, wherein the source is capable of emitting light comprising a second wavelength band associated with absorption by water, wherein the second wavelength band is less absorbed by water than the first wavelength band.

4. The water detector of claim 3, wherein the detector is configured to detect attenuation of the second wavelength band upon the light passing through the at least the portion of the flow stream instead of or in addition to the first wavelength band once the presence of water has been determined.

5. The water detector of claim 3, wherein the first wavelength band is around 1950 nm and the second wavelength band is around 1450 nm.

6. The water detector of claim 1, wherein the output is configured to adjust an amount of hydrate inhibitor based on the concentration of the water.

7. The water detector of claim 1, wherein the output comprises at least one of an alarm, a visual output, or an automated corrective action.

8. The water detector of claim 7, wherein the automated corrective action comprises a reduction in producing rate or in hydrate inhibitor injection.

9. The water detector of claim 1, wherein the source for emitting the light is a broadband light source.

10. The water detector of claim 1, wherein the light after passing through the at least the portion of the flow stream is received by groups of optical fibers, wherein individual optical fibers within at least one of the groups of optical fibers are arranged such that each individual fiber receives light transmitted across a discrete light path, through the at least the portion of the flow stream, that is different from a light path of adjacent fibers.

11. An optical water detector for monitoring a hydrocarbon well, comprising:
a source for emitting into a flow stream light that includes a first wavelength band associated with absorption by water;
a detector configured to detect attenuation of the first wavelength band upon the light passing through at least a portion of the flow stream; and
an output indicative of a concentration of water as determined based on the attenuation of the first wavelength band, wherein the output is configured to adjust an amount of hydrate inhibitor based on the concentration of water.

12. The water detector of claim 11, wherein the detector is configured to detect attenuation of the second wavelength band instead of or in addition to the first wavelength band when the concentration of the water is higher than a certain level.

13. A method of detecting water within a flow stream of a hydrocarbon well, comprising:
emitting into the flow stream light including first and second wavelength bands associated with absorption by water, wherein the second wavelength band is less absorbed by water than the first wavelength band;
detecting attenuation of the first wavelength band upon the light passing through at least a portion of the flow stream;
determining a concentration of water based on the attenuation of the first wavelength band; and
detecting attenuation of the second wavelength band instead of or in addition to the first wavelength band when the concentration of water is higher than a certain level.

14. The method of claim 13, further comprising disposing a water detector along a conduit containing the flow stream of the hydrocarbon well.

15. The method of claim 13, further comprising detecting attenuation of the second wavelength band upon the light passing through the at least the portion of the flow stream instead of or in addition to the first wavelength band once the presence of the water has been determined.

16. The method of claim 13, wherein the first wavelength band is around 1950 nm and the second wavelength band is around 1450 nm.

17. The method of claim 13, further comprising adjusting an operating parameter of the well upon determining water is present.

18. The method of claim 17, wherein adjusting the operating parameter comprises one of adjusting a production rate or adjusting injection of the hydrate inhibitor.

19. The method of claim 13, wherein the light after passing through the at least the portion of the flow stream is received by groups of optical fibers, wherein individual optical fibers within at least one of the groups of optical fibers are arranged such that each individual fiber receives light transmitted across a discrete light path, through the at least the portion of the flow stream, that is different from a light path of adjacent fibers.

* * * * *